(12) United States Patent
Rowe et al.

(10) Patent No.: US 11,696,821 B2
(45) Date of Patent: Jul. 11, 2023

(54) ASYMMETRIC ELECTRODE INSULATION FOR ARTIFICIAL MUSCLES

(71) Applicant: Toyota Motor Engineering & Manufacturing North America, Inc., Plano, TX (US)

(72) Inventors: Michael P. Rowe, Pinckney, MI (US); Maduran Palaniswamy, Ann Arbor, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 281 days.

(21) Appl. No.: 17/218,287

(22) Filed: Mar. 31, 2021

(65) Prior Publication Data

US 2022/0313420 A1 Oct. 6, 2022

(51) Int. Cl.
*F15B 15/10* (2006.01)
*F15B 21/06* (2006.01)
(Continued)

(52) U.S. Cl.
CPC ............... *A61F 2/08* (2013.01); *B25J 9/1095* (2013.01); *F15B 15/103* (2013.01); *F15B 21/06* (2013.01); *F03G 7/00* (2013.01)

(58) Field of Classification Search
CPC .. F03G 7/00; B25J 9/1095; B25J 9/142; B25J 9/1075; F15B 15/00; F15B 15/103
See application file for complete search history.

(56) References Cited

U.S. PATENT DOCUMENTS

| 7,133,273 B2 | 11/2006 | Ferreres |
| 9,164,277 B2 | 10/2015 | Conrad et al. |
| 2020/0032822 A1* | 1/2020 | Keplinger ............ F15B 21/065 |

FOREIGN PATENT DOCUMENTS

| CN | 110253612 A | 9/2019 |
| JP | 5416904 B2 | 2/2014 |

(Continued)

OTHER PUBLICATIONS

E. Acome, et al., "Hydraulically Amplified Self-Healing Electrostatic Actuators With Muscle-Like Performance," Science Journal, Jan. 5, 2018: vol. 359, Issue 6371, pp. 61-651, Department of Mechanical Engineering & Materials Science and Engineering Program, University of Colorado, Boulder, CO 80309, USA.

*Primary Examiner* — Abiy Teka
*Assistant Examiner* — Daniel S Collins
(74) *Attorney, Agent, or Firm* — Dinsmore & Shohl LLP

(57) ABSTRACT

An artificial muscle that includes a housing having an electrode region and an expandable fluid region, a dielectric fluid housed within the housing, an electrode pair positioned in the electrode region of the housing, the electrode pair including a first electrode and a second electrode, and an electrode insulator having one or more insulation layers. The electrode insulator is disposed on an inner electrode surface of the first electrode of the electrode pair. The second electrode includes a free inner electrode surface exposed to the dielectric fluid when the electrode pair is in a non-actuated state. The electrode pair is actuatable between the non-actuated state and an actuated state such that actuation from the non-actuated state to the actuated state directs the dielectric fluid into the expandable fluid region, expanding the expandable fluid region.

20 Claims, 8 Drawing Sheets

(51) Int. Cl.
    *A61F 2/08*     (2006.01)
    *B25J 9/10*     (2006.01)
    *F03G 7/00*     (2006.01)

(56)     References Cited

FOREIGN PATENT DOCUMENTS

| | | | | |
|---|---|---|---|---|
| KR | 101610794 | B1 | 4/2016 | |
| WO | 2012155276 | A1 | 11/2012 | |
| WO | WO-2020180982 | A1 * | 9/2020 | ............. B32B 27/08 |

\* cited by examiner

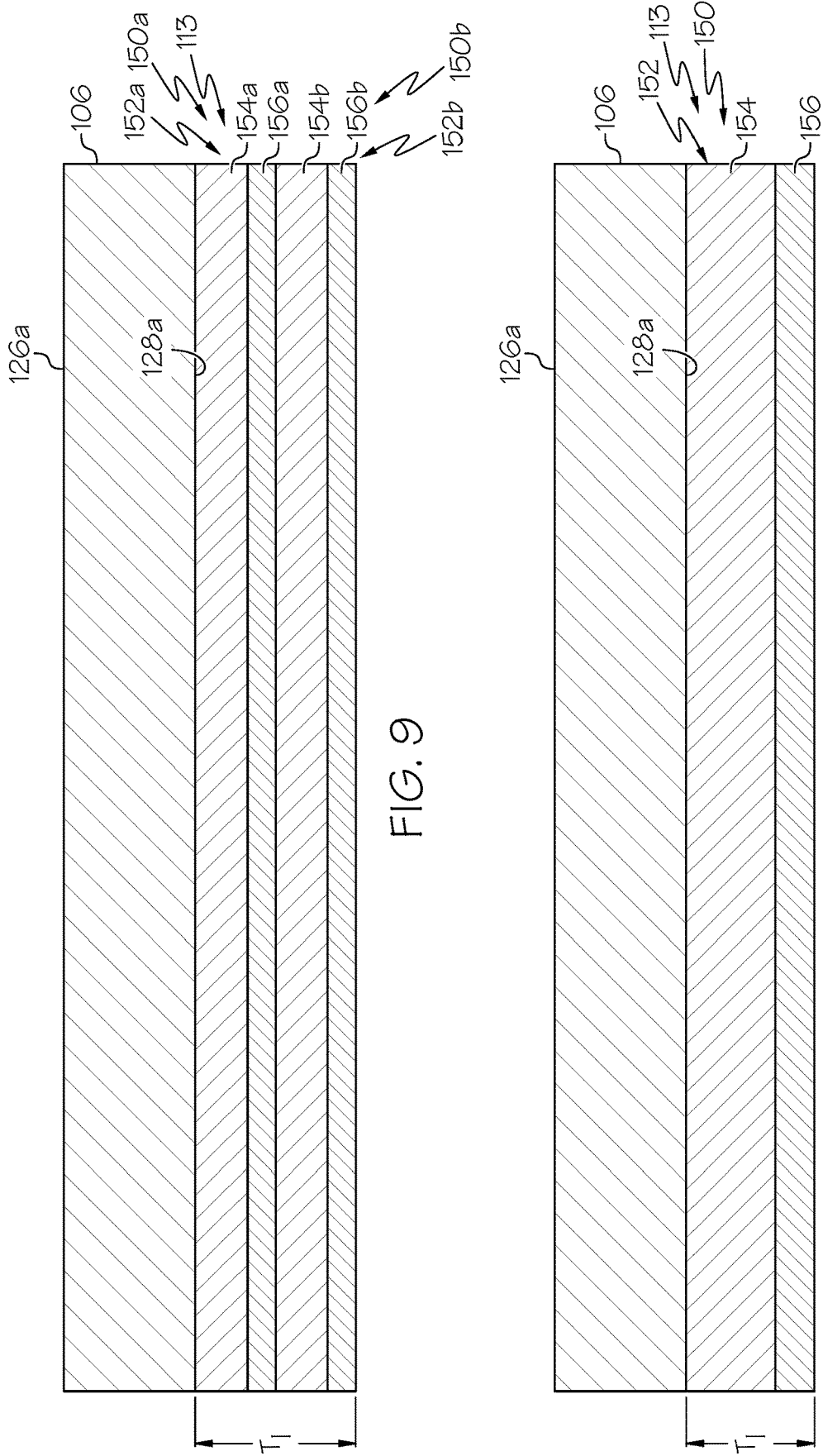

ASYMMETRIC ELECTRODE INSULATION FOR ARTIFICIAL MUSCLES

TECHNICAL FIELD

The present specification generally relates artificial muscles having electrode pairs with asymmetric electrode insulation.

BACKGROUND

Current artificial muscles have an equal amount of electrical insulation on each electrode. However, with equal amounts of electrical insulation, current artificial muscles have an electrical voltage breakdown failure rate that increases as loads increase. In some situations, even if the artificial muscle produces enough electrostatic force to lift a large weight (such as a 1 kg or greater weight), the stress induced reduction of polymer insulation electrical breakdown voltage may cause the artificial muscle to fail via electrical short. In other words, the material properties of current artificial muscles do not scale with scaled-up electrostatic force production via increased electrode size.

Accordingly, a need exists for alternative artificial muscles with improved electrical breakdown voltage to facilitate scaled-up electrostatic force production.

SUMMARY

In one embodiment, an artificial muscle includes a housing having an electrode region and an expandable fluid region, a dielectric fluid housed within the housing, an electrode pair positioned in the electrode region of the housing, the electrode pair including a first electrode and a second electrode, and an electrode insulator having one or more insulation layers. The electrode insulator is disposed on an inner electrode surface of the first electrode of the electrode pair. The second electrode includes a free inner electrode surface exposed to the dielectric fluid when the electrode pair is in a non-actuated state. The electrode pair is actuatable between the non-actuated state and an actuated state such that actuation from the non-actuated state to the actuated state directs the dielectric fluid into the expandable fluid region, expanding the expandable fluid region.

In another embodiment, a method for actuating an artificial muscle includes providing a voltage using a power supply electrically coupled to an electrode pair of an artificial muscle, the artificial muscle including a housing having an electrode region and an expandable fluid region, where the electrode pair is housed within the electrode region of the housing and includes a first electrode and a second electrode, a dielectric fluid housed within the housing, and an electrode insulator having one or more insulation layers, where the electrode insulator is disposed on an inner electrode surface of the first electrode and the second electrode includes a free inner electrode surface exposed to the dielectric fluid when the electrode pair is in a non-actuated state. The method also includes applying the voltage to the electrode pair of the artificial muscle, thereby actuating the electrode pair from the non-actuated state to an actuated state such that the dielectric fluid is directed into the expandable fluid region of the housing and expands the expandable fluid region.

In yet another embodiment, an artificial muscle includes a housing having an electrode region and an expandable fluid region, a dielectric fluid housed within the housing, an electrode pair positioned in the electrode region of the housing, the electrode pair having a first electrode and a second electrode, and an electrode insulator having one or more insulation layers. The electrode insulator is disposed on an inner electrode surface of the first electrode, the second electrode includes a free inner electrode surface facing the electrode insulator and the electrode pair is actuatable between a non-actuated state and an actuated state such that actuation from the non-actuated state to the actuated state directs the dielectric fluid into the expandable fluid region, expanding the expandable fluid region.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 9 schematically depicts an example electrode having an electrode insulator disposed thereon, the insulator comprising two insulation bilayers, according to one or more embodiments shown and described herein;

FIG. 10 schematically depicts an example electrode having an insulator disposed thereon, the insulator comprising a single insulation bilayer, according to one or more embodiments shown and described herein.

DETAILED DESCRIPTION

Figure 1:
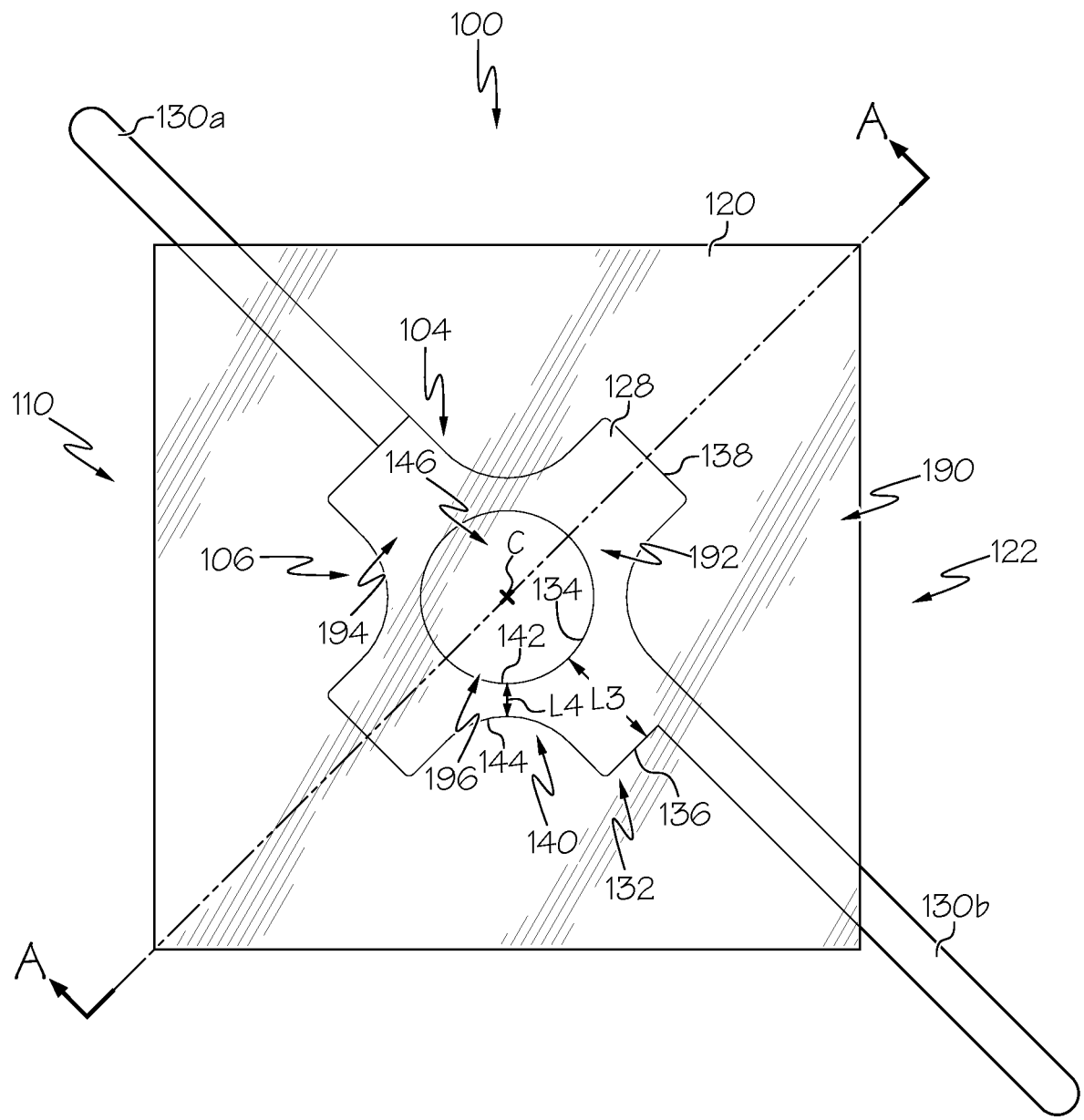
FIG. 1 schematically depicts a top view of one example artificial muscle, according to one or more embodiments shown and described herein.

Embodiments described herein are directed to artificial muscles that are actuatable to selectively raise and lower a region of the artificial muscles to provide a selective, on demand inflated expandable fluid region. The artificial muscles each include an electrode pair comprising a first electrode and a second electrode that may be drawn together by application of a voltage, thereby pushing dielectric fluid into the expandable fluid region. In addition, some embodiments of the artificial muscles described herein include an asymmetric electrode insulator configured to mitigate electrical breakdown voltage reduction when the electrode insulator is under stress. The asymmetric electrode insulator fortifies the artificial muscle against electrical shorting, allowing the artificial muscle to operate under increased voltages, increasing the actuation power of the artificial muscles, allowing the artificial muscle to reliably lift more weight. In particular, embodiments of the artificial muscles described herein achieve this asymmetry with an electrode insulator that is disposed on an inner electrode surface of the first electrode, while the inner electrode surface of the second electrode is a free surface. That is, the inner electrode surface of the second electrode faces the electrode insulator and is exposed to dielectric fluid when the artificial muscle is in a non-actuated state. Various embodiments of artificial muscles are described in more detail herein. Whenever possible, the same reference numerals will be used throughout the drawings to refer to the same or like parts.

Referring now to FIGS. 1-8, artificial muscles 100, 100' are schematically depicted in a number of views. The artificial muscles 100, 100' each include an electrode pair 104 disposed in a housing 110 together with a dielectric fluid 198. The electrode pair 104 comprises a first electrode 106 and a second electrode 108 and the electrode pair 104 is disposed in an electrode region 194 of the housing 110, adjacent an expandable fluid region 196. In operation, voltage may be applied to the electrode pair 104, drawing the electrode pair 104 together, which directs dielectric fluid into the expandable fluid region 196, expanding the expandable fluid region 196.

The artificial muscle 100 of FIGS. 1-4 includes a first electrode insulator 111 disposed on the first electrode 106 and a second electrode insulator 112 disposed on the second electrode 108, while the artificial muscle 100' of FIGS. 5-8 includes an electrode insulator 113 (e.g., a single electrode insulator) disposed on the first electrode 106. An inner electrode surface 128b of the second electrode 108 of the artificial muscle 100' is a free surface, which creates insulator asymmetry in the artificial muscle 100'. The single electrode insulator 113 has a greater thickness than each of the first electrode insulator 111 and the second electrode insulator 112, individually, but may comprise a thickness that is equal to the collective thickness of the first and second electrode insulators 111, 112.

Figure 2:
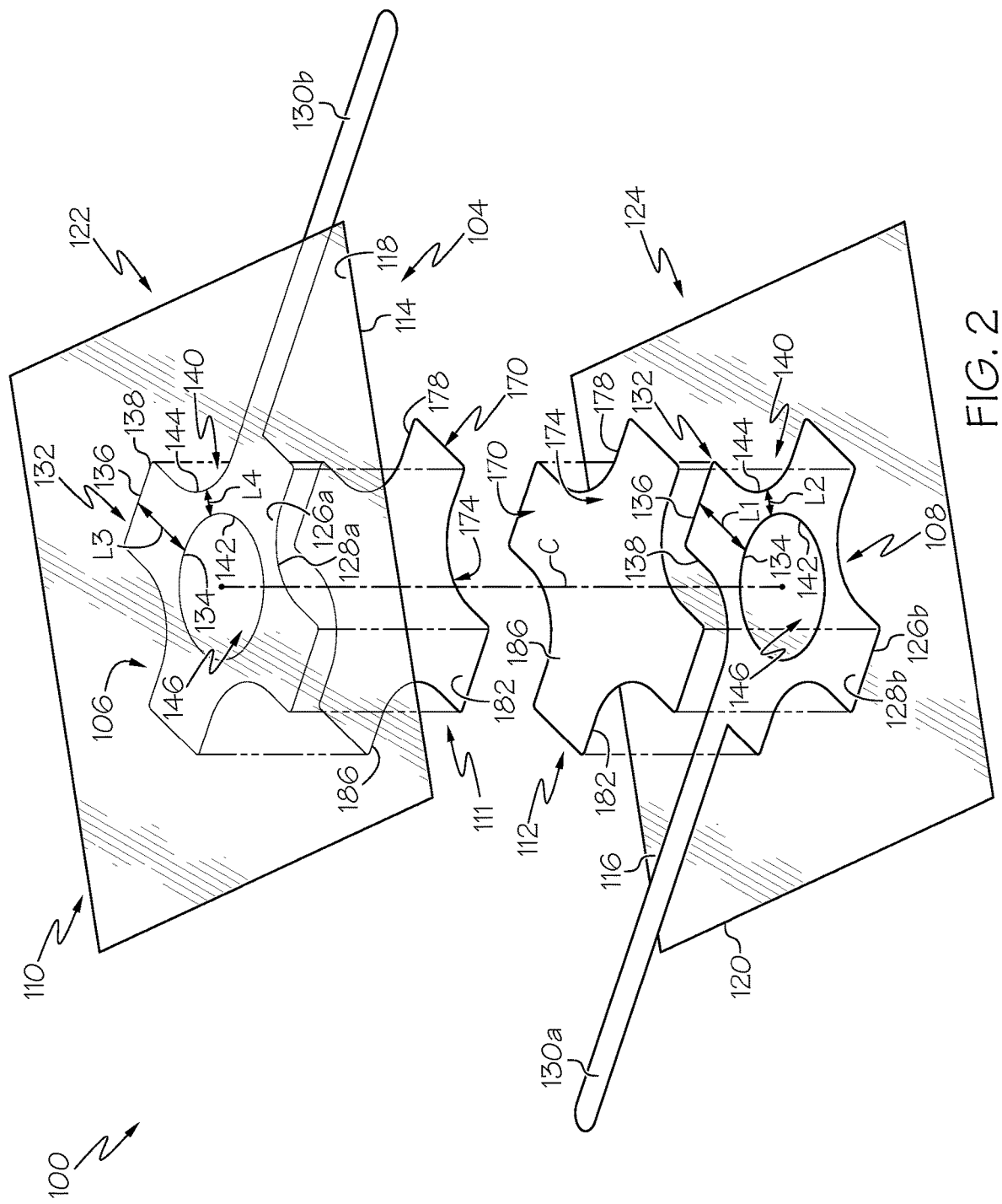
FIG. 2 schematically depicts an exploded view of the artificial muscle of FIG. 1, according to one or more embodiments shown and described herein.

Referring now to FIGS. 1 and 2, the artificial muscle 100 is depicted in more detail. The artificial muscle 100 includes the housing 110, the electrode pair 104, including the first electrode 106 and the second electrode 108, which may be fixed to opposite surfaces of the housing 110, the first electrode insulator 111 fixed to the first electrode 106, and the second electrode insulator 112 fixed to the second electrode 108. In some embodiments, the housing 110 is a one-piece monolithic layer including a pair of opposite inner surfaces, such as a first inner surface 114 and a second inner surface 116, and a pair of opposite outer surfaces, such as a first outer surface 118 and a second outer surface 120. In some embodiments, the first inner surface 114 and the second inner surface 116 of the housing 110 are heat-sealable. In other embodiments, the housing 110 may be a pair of individually fabricated film layers, such as a first film layer 122 and a second film layer 124. Thus, the first film layer 122 includes the first inner surface 114 and the first outer surface 118, and the second film layer 124 includes the second inner surface 116 and the second outer surface 120.

While the embodiments described herein primarily refer to the housing 110 as comprising the first film layer 122 and the second film layer 124, as opposed to the one-piece housing, it should be understood that either arrangement is contemplated. In some embodiments, the first film layer 122 and the second film layer 124 generally include the same structure and composition. For example, in some embodiments, the first film layer 122 and the second film layer 124 each comprises biaxially oriented polypropylene (BOPP).

The first electrode 106 and the second electrode 108 are each positioned between the first film layer 122 and the second film layer 124. In some embodiments, the first electrode 106 and the second electrode 108 are each aluminum-coated polyester such as, for example, Mylar®. In addition, one of the first electrode 106 and the second electrode 108 is a negatively charged electrode and the other of the first electrode 106 and the second electrode 108 is a positively charged electrode. For purposes discussed herein, either electrode 106, 108 may be positively charged so long as the other electrode 106, 108 of the artificial muscle 100 is negatively charged.

Figure 11:
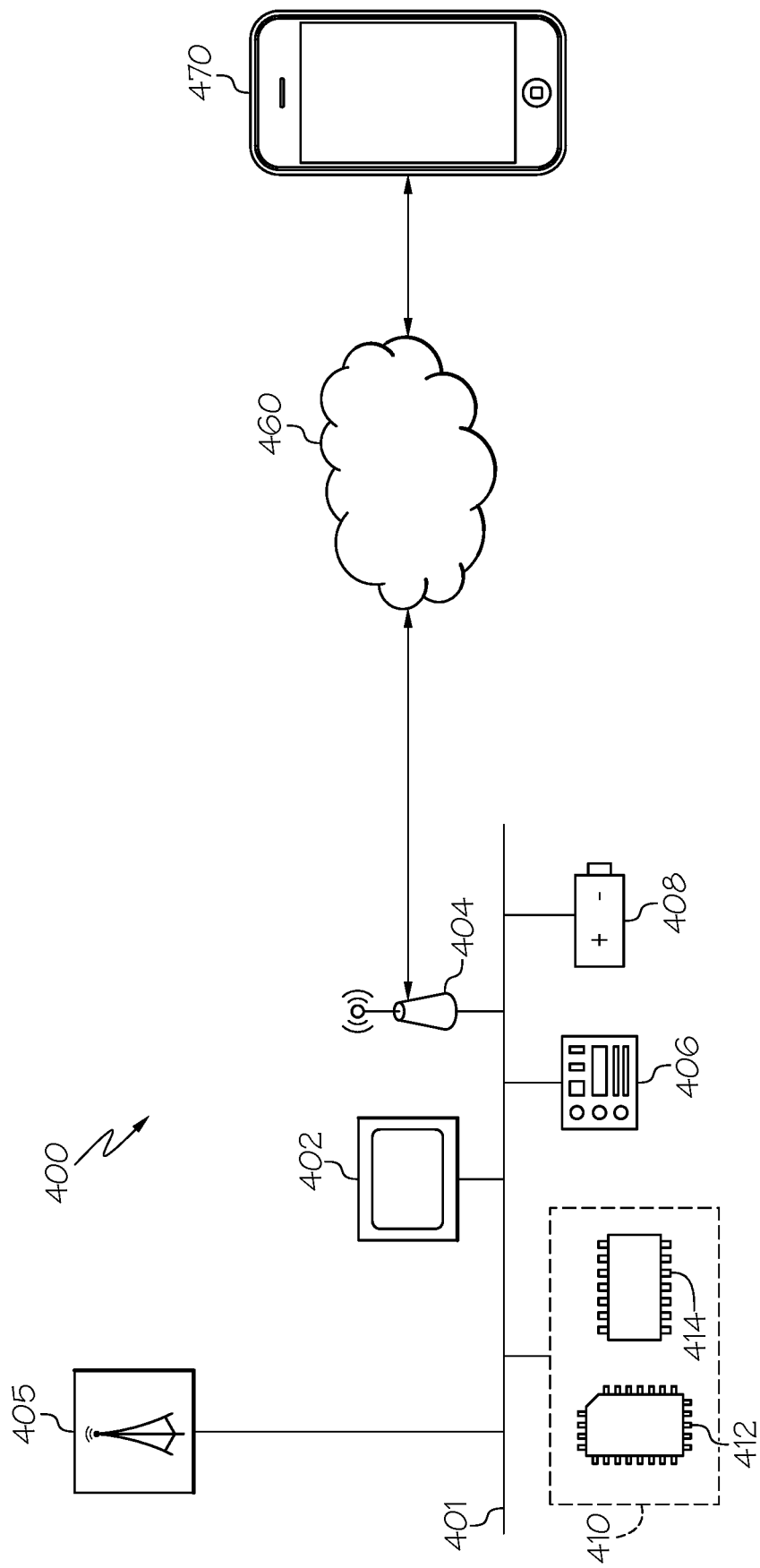
FIG. 11 schematically depicts an actuation system for operating the artificial muscles of FIGS. 1-8, according to one or more embodiments shown and described herein.

The first electrode 106 has a film-facing electrode surface 126a and an inner electrode surface 128a. The first electrode 106 is positioned against the first film layer 122, specifically, the first inner surface 114 of the first film layer 122. In addition, the first electrode 106 includes a first terminal 130a extending from the first electrode 106 past an edge of the first film layer 122 such that the first terminal 130a can be connected to a power supply to actuate the first electrode 106. Specifically, the terminal is coupled, either directly or in series, to a power supply 408 and a controller 410 of an actuation system 400, as shown in FIG. 11. Similarly, the second electrode 108 has a film-facing electrode surface 126b and an inner electrode surface 128b. The second electrode 108 is positioned against the second film layer 124, specifically, the second inner surface 116 of the second film layer 124. The second electrode 108 includes a second terminal 130b extending from the second electrode 108 past an edge of the second film layer 124 such that the second terminal 130b can be connected to a power supply 408 and a controller 410 of the actuation system 400 to actuate the second electrode 108.

The first electrode 106 and the second electrode 108 each comprise two or more tab portions 132 and two or more bridge portions 140. Each bridge portion 140 is positioned between adjacent tab portions 132, interconnecting these adjacent tab portions 132. Each tab portion 132 has a first end 134 extending radially from a center axis C of the first electrode 106 to an opposite second end 136 of the tab portion 132, where the second end 136 defines a portion of an outer perimeter 138 of the first electrode 106. Each bridge portion 140 has a first end 142 extending radially from the center axis C of the first electrode 106 to an opposite second end 144 of the bridge portion 140 defining another portion of the outer perimeter 138 of the first electrode 106. Each tab portion 132 has a tab length L1 and each bridge portion 140 has a bridge length L2 extending in a radial direction from the center axis C of the first electrode 106. The tab length L1 is a distance from the first end 134 to the second end 136 of the tab portion 132 and the bridge length L2 is a distance from the first end 142 to the second end 144 of the bridge portion 140. The tab length L1 of each tab portion 132 is longer than the bridge length L2 of each bridge portion 140.

In some embodiments, the bridge length L2 is 20% to 50% of the tab length L1, such as 30% to 40% of the tab length L1.

In some embodiments, the two or more tab portions 132 are arranged in one or more pairs of tab portions 132. Each pair of tab portions 132 includes two tab portions 132 arranged diametrically opposed to one another. In some embodiments, the first electrode 106 and the second electrode 108 may include only two tab portions 132 positioned on opposite sides or ends of the first electrode 106. In some embodiments, as shown in FIGS. 1 and 2, the first electrode 106 and the second electrode 108 each include four tab portions 132 and four bridge portions 140 interconnecting adjacent tab portions 132. In this embodiment, the four tab portion 132 are arranged as two pairs of tab portions 132 diametrically opposed to one another. Furthermore, as shown, the first terminal 130a extends from the second end 136 of one of the tab portions 132 and is integrally formed therewith. Due to the first electrode 106 and the second electrode 108 being coaxial with one another, the center axis C of the first electrode 106 and the second electrode 108 are the same.

Figure 3:
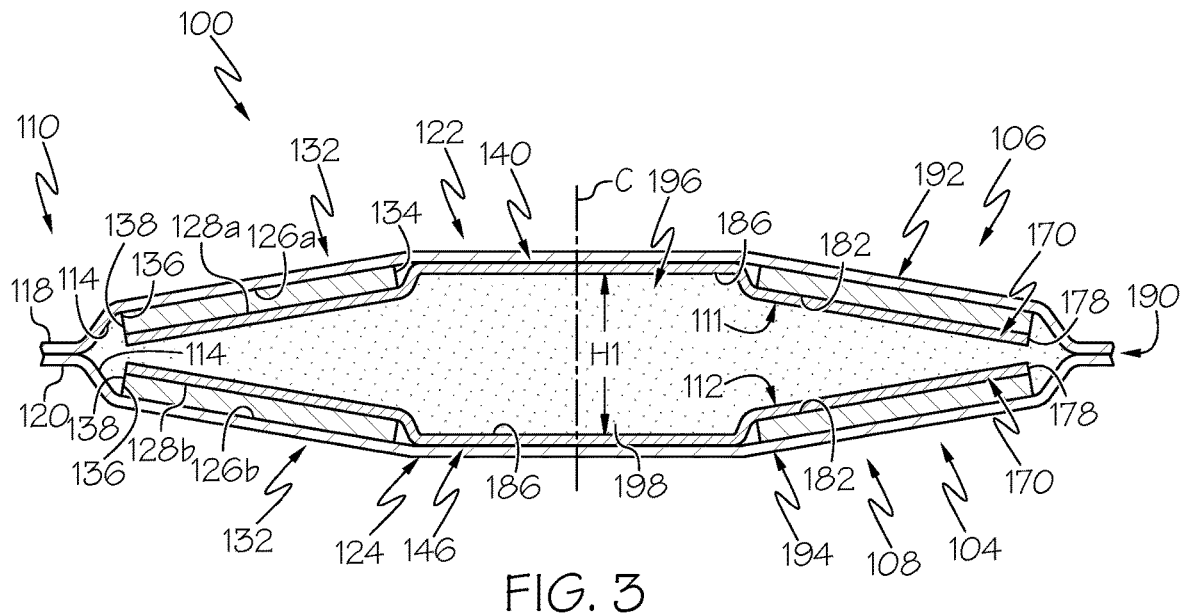
FIG. 3 schematically depicts a cross-sectional view of the artificial muscle of FIGS. 1 and 2, taken along line A-A of FIG. 1, in a non-actuated state, according to one or more embodiments shown and described herein.
Figure 4:
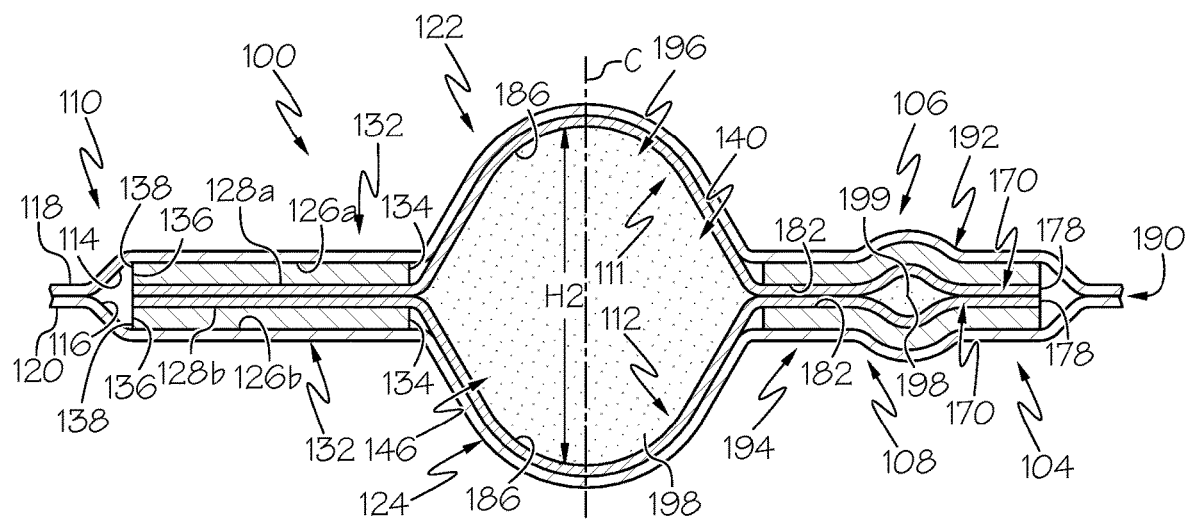
FIG. 4 schematically depicts a cross-sectional view of the artificial muscle of FIGS. 1 and 2 taken along line A-A of FIG. 1, in an actuated state, according to one or more embodiments shown and described herein.
Figure 5:
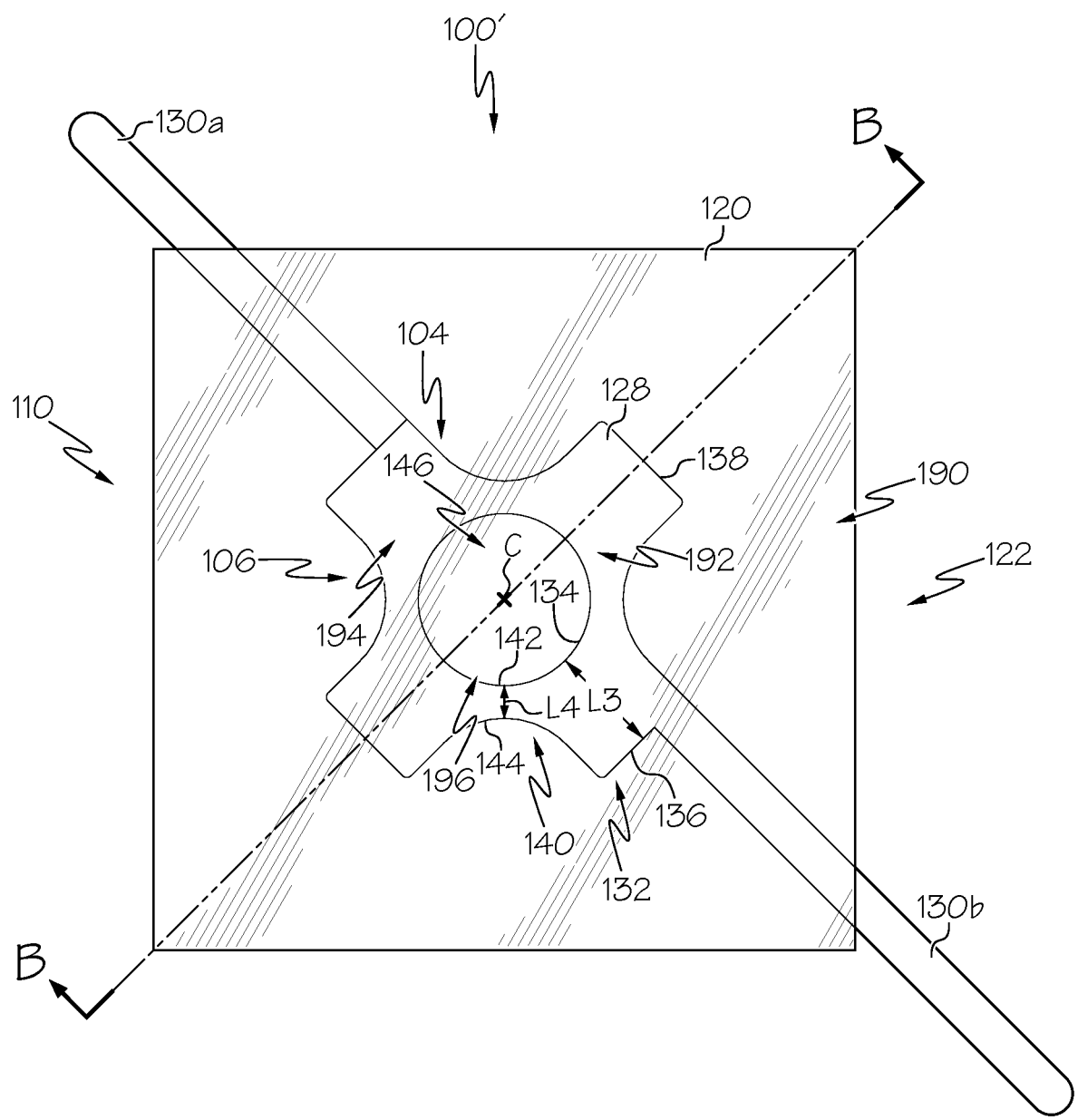
FIG. 5 schematically depicts a top view of another example artificial muscle, according to one or more embodiments shown and described herein.
Figure 6:
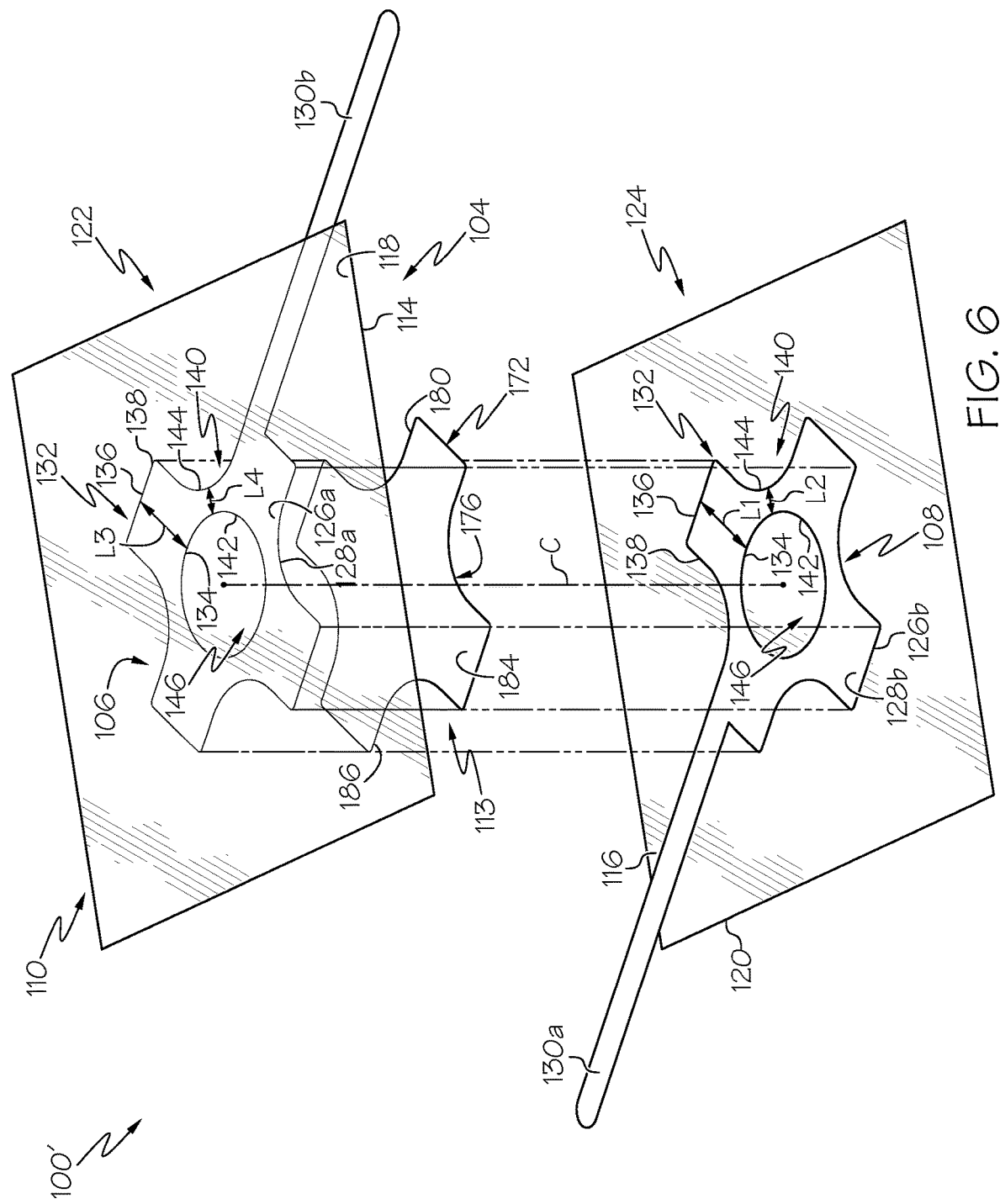
FIG. 6 schematically depicts an exploded view of the artificial muscle of FIG. 5, according to one or more embodiments shown and described herein.

Referring still to FIGS. 1-4, at least one of the first electrode 106 and the second electrode 108 has a central opening formed therein between the first end 134 of the tab portions 132 and the first end 142 of the bridge portions 140. As shown in FIGS. 3 and 4, the first electrode 106 and the second electrode 108 each have a central opening 146. However, it should be understood that the first electrode 106 does not need to include the central opening 146 when a central opening is provided within the second electrode 108. Alternatively, the second electrode 108 does not need to include the central opening when the central opening 146 is provided within the first electrode 106.

Referring still to FIGS. 1-4, the first electrode insulator 111 and the second electrode insulator 112 have a geometry generally corresponding to the first electrode 106 and the second electrode 108, respectively. Thus, the first electrode insulator 111 and the second electrode insulator 112 each have tab portions 170 and bridge portions 174 corresponding to like portions on the first electrode 106 and the second electrode 108. Further, the first electrode insulator 111 and the second electrode insulator 112 each have an outer perimeter 178 corresponding to the outer perimeter 138 of the first electrode 106 and the second electrode 108, respectively, when positioned thereon.

It should be appreciated that, in some embodiments, the first electrode insulator 111 and the second electrode insulator 112 generally include the same structure and composition. As such, in some embodiments, the first electrode insulator 111 and the second electrode insulator 112 each include an adhesive surface 182 and an opposite non-sealable surface 186, respectively. Thus, in some embodiments, the first electrode insulator 111 and the second electrode insulator 112 are each a polymer tape adhered to the inner electrode surface 128a, 128b of the first electrode 106 and the second electrode 108, respectively.

Referring now to FIGS. 1-4, the artificial muscle 100 is shown in its assembled form with the first terminal 130a of the first electrode 106 and the second terminal 130b of the second electrode 108 extending past an outer perimeter of the housing 110, i.e., the first film layer 122 and the second film layer 124. As shown in FIG. 1, the first electrode 106 is stacked on top of the second electrode 108 and, therefore, the second electrode 108 and the second film layer 124 are not shown. In its assembled form, the first electrode 106, the second electrode 108, the first electrode insulator 111, and the second electrode insulator 112 are sandwiched between the first film layer 122 and the second film layer 124. The first film layer 122 is partially sealed to the second film layer 124 at an area surrounding the outer perimeter 138 of the first electrode 106 and the second electrode 108. In some embodiments, the first film layer 122 is heat-sealed to the second film layer 124. Specifically, in some embodiments, the first film layer 122 is sealed to the second film layer 124 to define a sealed portion 190 surrounding the first electrode 106 and the second electrode 108. The first film layer 122 and the second film layer 124 may be sealed in any suitable manner, such as using an adhesive, heat sealing, or the like.

The first electrode 106, the second electrode 108, the first electrode insulator 111, and the second electrode insulator 112 provide a barrier that prevents the first film layer 122 from sealing to the second film layer 124 forming an unsealed portion 192. The unsealed portion 192 of the housing 110 includes the electrode region 194, in which the electrode pair 104 is provided, and the expandable fluid region 196, which is surrounded by the electrode region 194. The central openings 146 of the first electrode 106 and the second electrode 108 form the expandable fluid region 196 and are arranged to be axially stacked on one another. Although not shown, the housing 110 may be cut to conform to the geometry of the electrode pair 104 and reduce the size of the artificial muscle 100, namely, the size of the sealed portion 190.

A dielectric fluid 198 is provided within the unsealed portion 192 and flows freely between the first electrode 106 and the second electrode 108. A "dielectric" fluid as used herein is a medium or material that transmits electrical force without conduction and as such has low electrical conductivity. Some non-limiting example dielectric fluids include perfluoroalkanes, transformer oils, and deionized water. It should be appreciated that the dielectric fluid 198 may be injected into the unsealed portion 192 of the artificial muscle 100 using a needle or other suitable injection device.

Referring now to FIGS. 3 and 4, the artificial muscle 100 is actuatable between a non-actuated state and an actuated state. In the non-actuated state, as shown in FIG. 3, the first electrode 106 and the second electrode 108 are partially spaced apart from one another proximate the central openings 146 thereof and the first end 134 of the tab portions 132. The second end 136 of the tab portions 132 remain in position relative to one another due to the housing 110 being sealed at the outer perimeters 138 of the first electrode 106 and the second electrode 108. When transitioning to the actuated state, which is shown in FIG. 4, the first electrode 106 and the second electrode 108 are brought into contact with and oriented parallel to one another to force the dielectric fluid 198 into the expandable fluid region 196. This causes the dielectric fluid 198 to flow through the central openings 146 of the first electrode 106 and the second electrode 108 and inflate the expandable fluid region 196.

Referring now to FIG. 3, the artificial muscle 100 is shown in the non-actuated state. The electrode pair 104 is provided within the electrode region 194 of the unsealed portion 192 of the housing 110. The central opening 146 of the first electrode 106 and the second electrode 108 are coaxially aligned within the expandable fluid region 196. In the non-actuated state, the first electrode 106 and the second electrode 108 are partially spaced apart from and non-parallel to one another. Due to the first film layer 122 being sealed to the second film layer 124 around the electrode pair 104, the second end 136 of the tab portions 132 are brought into contact with one another. Thus, dielectric fluid 198 is provided between the first electrode 106 and the second electrode 108, thereby separating the first end 134 of the tab portions 132 proximate the expandable fluid region 196. Stated another way, a distance between the first end 134 of the tab portion 132 of the first electrode 106 and the second electrode 108 is greater than a distance between the second end 136 of the tab portion 132 of the first electrode 106 and the second electrode 108. This results in the electrode pair 104 zippering toward the expandable fluid region 196 when actuated. In some embodiments, the first electrode 106 and the second electrode 108 may be flexible. Thus, as shown in FIG. 3, the first electrode 106 and the second electrode 108 are convex such that the second ends 136 of the tab portions 132 thereof may remain close to one another, but spaced apart from one another proximate the central openings 146. In the non-actuated state, the expandable fluid region 196 has a first height H1.

When actuated, the first electrode 106 and the second electrode 108 zipper toward one another from the second ends 144 of the tab portions 132, thereof, thereby pushing the dielectric fluid 198 into the expandable fluid region 196. As shown in FIG. 4, when in the actuated state, the first electrode 106 and the second electrode 108 are parallel to one another. In the actuated state, the dielectric fluid 198 flows into the expandable fluid region 196 to inflate the expandable fluid region 196. As such, the first film layer 122 and the second film layer 124 expand in opposite directions. In the actuated state, the expandable fluid region 196 has a second height H2, which is greater than the first height H1 of the expandable fluid region 196 when in the non-actuated state. Although not shown, it should be noted that the electrode pair 104 may be partially actuated to a position between the non-actuated state and the actuated state. This would allow for partial inflation of the expandable fluid region 196 and adjustments when necessary.

Referring still to FIG. 4, during actuation of the artificial muscle 100, one or more dielectric fluid pockets 199 may form between the electrode pair 104. In some situations, the one or more dielectric fluid pockets 199 may be temporarily present as the artificial muscle 100 actuates from the non-actuated state to the actuated state such that the dielectric fluid 198 disposed in the one or more dielectric fluid pockets 199 eventually migrates to the expandable fluid region 196 while the artificial muscle 100 remains in the actuated state. In other situations, the one or more dielectric fluid pockets 199 may remain present until the artificial muscle 100 is actuated from the actuated state back to the non-actuated state. In operation, the dielectric fluid pockets 199 form a hotspot for stress induced electrical breakdown of the electrode pair 104. In other words, if the voltage applied to the electrode pair 104 to actuate the electrode pair 104 is greater than the electrical breakdown voltage of each of the first electrode insulator 111 and the second electrode insulator 112 at the dielectric fluid pocket 199, an electrical short may occur. While not intending to be limited by theory, the shape alteration of the first and second electrode insulator 111, 112 at the dielectric fluid pocket 199 (e.g., localized material expansion and/or localized material compression) creates a mechanical stress on the polymer material of both the first and second electrode insulators 111, 112 reducing the electrical breakdown voltage of the material of each of the first and second electrode insulator 111, 112, increasing the likelihood that the voltage applied to the electrode pair 104 is greater than this reduced electrical breakdown voltage of the first and second electrode insulator 111, 112 at the dielectric fluid pocket 199. Electrical shorting caused by stress induced reduction of the electrical breakdown voltage of each of the first and second electrode insulators 111, 112 causes unwanted failures of the artificial muscle 100, particularly as the voltage applied to the artificial muscles 100 increases to lift or otherwise translate larger loads.

Referring now to FIGS. 5-8, the artificial muscle 100' is illustrated. The artificial muscle 100' is similar to the artificial muscle 100. As such, like structure is indicated with like reference numerals. However, as shown, the artificial muscle 100' includes the electrode insulator 113 (e.g., a single electrode insulator) disposed on the inner electrode surface 128a of the first electrode 106 and does not include an electrode insulator (such as the second electrode insulator 112 of FIGS. 1-4) disposed on the inner electrode surface 128b of the second electrode 108. Instead, the inner electrode surface 128b is a free inner electrode surface. That is, the free inner electrode surface 128b is exposed to the dielectric fluid 198 when the electrode pair 104 is in the non-actuated state. Indeed, the free inner electrode surface 128b of the second electrode 108 may be in an orientation facing the electrode insulator 113 in both the actuated state and the non-actuated state of the electrode pair 104. Moreover, when the electrode pair 104 is in the actuated state, the electrode insulator 113 contacts the free inner electrode surface 128b of the second electrode 108.

Figure 7:
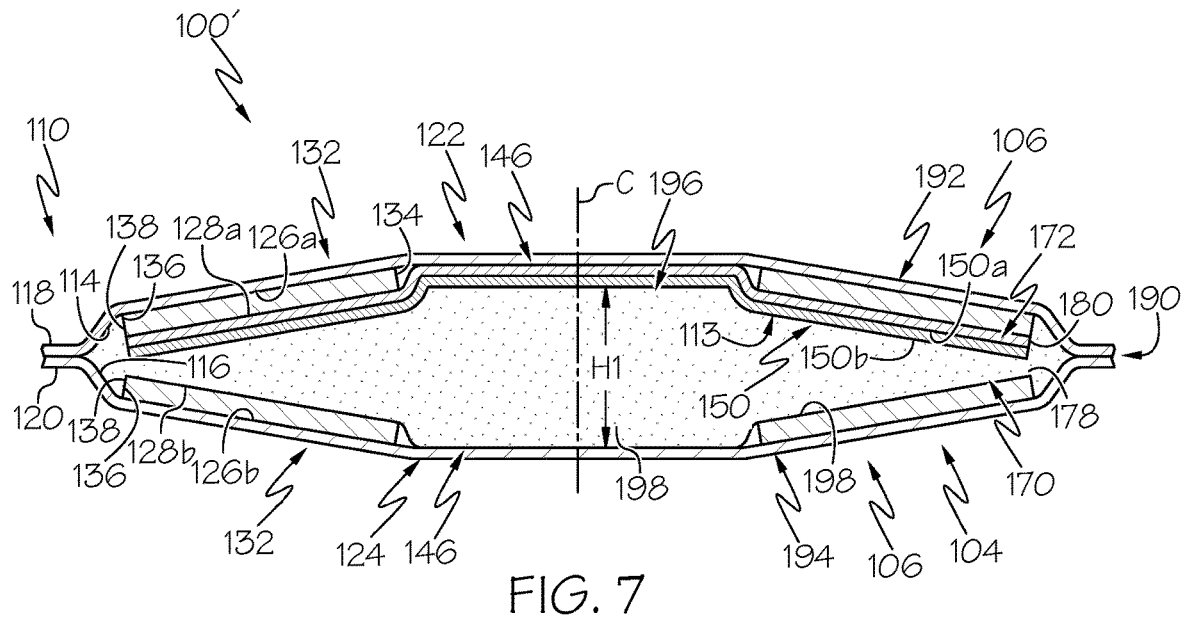
FIG. 7 schematically depicts a cross-sectional view of the artificial muscle of FIGS. 5 and 6, taken along line B-B of FIG. 5, in a non-actuated state, according to one or more embodiments shown and described herein.
Figure 8:
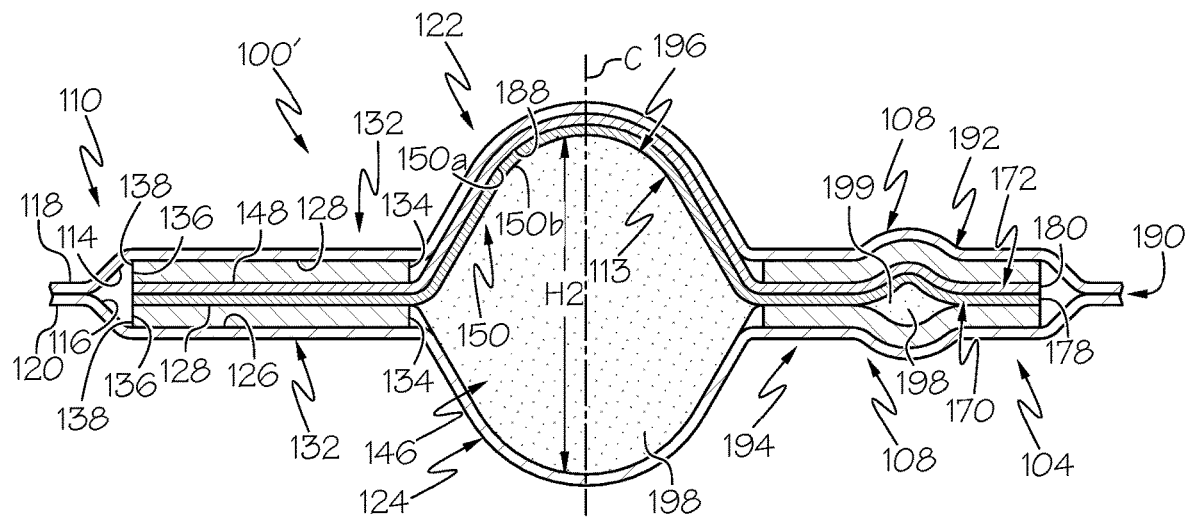
FIG. 8 schematically depicts a cross-sectional view of the artificial muscle of FIGS. 5 and 6 taken along line B-B of FIG. 5, in an actuated state, according to one or more embodiments shown and described herein.

Referring still to FIGS. 5-8, the electrode insulator 113 comprises one or more insulation layers 150 and is disposed on the inner electrode surface 128a of the first electrode 106. The electrode insulator 113 has a geometry generally corresponding to the first electrode 106 and the second electrode 108. Thus, the electrode insulator 113 includes tab portions 170 and bridge portions 174 corresponding to like portions on the first electrode 106 and the second electrode 108. The electrode insulator 113 also has an outer perimeter 178 corresponding to the outer perimeter 138 of the first electrode 106 when positioned thereon. Furthermore, while embodiments are described herein in which the electrode insulator 113 is disposed on the first electrode 106, it should be understood that embodiments are contemplated in which the electrode insulator 113 is disposed on the inner electrode surface 128b of the second electrode 108 and the inner electrode surface 128a of the first electrode 106 is a free inner electrode surface. In some embodiments, as depicted in FIGS. 7 and 8, the electrode insulator 113 comprises a plurality of insulation layers 150, such as a first insulation layer 150a disposed on the inner electrode surface 128a of the first electrode 106 and a second insulation layer 150b disposed on the first insulation layer 150a. Each insulation layer 150 may comprise one or more polymer materials.

Referring again to FIGS. 1-8, the electrode insulator 113 has a greater thickness than each of the first electrode insulator 111 and the second electrode insulator 112, individually, but may comprise a thickness that is equal to the collectively thickness of the first and second electrode insulators 111, 112. Thus, for comparison, the artificial muscles 100, 100' may have the same electrode insulation thickness and, assuming they comprise the same materials, the same electrical breakdown voltage. However, by positioning the electrode insulator 113 on the first electrode 106, such that the inner electrode surface 128b of the second electrode 108 is a free surface, the electrode insulator 113 is more resistant to the stress induced reduction of the electrical breakdown voltage that occurs when one or more dielectric fluid pockets 199 are formed during actuation.

Referring now to FIG. 8, a dielectric fluid pocket 199 is depicted in the artificial muscle 100'. As noted above with respect to FIG. 4, the dielectric fluid pocket 199 is a hotspot for stress induced electrical breakdown of the electrode pair 104. While not intending to be limited by theory, the shape alteration of the electrode insulator 113 at the dielectric fluid pocket 199 (e.g., localized material expansion and/or localized material compression) creates a mechanical stress on the material of the electrode insulator 113, reducing the electrical breakdown voltage of the material of the electrode insulator 113. However, because the electrode insulator 113 is disposed on a single electrode, the electrode insulator 113 undergoes equivalent mechanical stress at the dielectric fluid pocket 199 as each of the first and second electrodes 111, 112 (assuming equally sized and shaped dielectric fluid pockets 199 for the comparison). Thus, without intending to be limited by theory, the reduction of the electrical breakdown voltage of the electrode insulator 113 is equal to the reduction of the reduction of the electrical breakdown voltage of one of the first and second electrode insulators 111, 112. In other words, the stress induced reduction of the electrically breakdown voltage is halved by using the electrode insulator 113 when compared to the first and second electrode insulators 111, 112. This increases the effectiveness of the artificial muscle 100' at resisting stress-induced reduction of the electrical breakdown voltage. In operation, this allows the artificial muscle 100' to operate at increased voltages without failure, increasing the amount of force that the artificial muscle 100' may apply to a load.

Referring now to FIGS. 9 and 10, in some embodiments, the one or more insulation layers 150 of the electrode insulator 113 each comprise an insulation bilayer 152. In particular, each insulation bilayer 152 may comprise an acryl-based polymer layer 154, such as poly(ethylacrylate acrylamide), and a biaxially oriented polypropylene (BOPP) layer 156. The insulation bilayer 152 comprises a high breakdown voltage per thickness and thus facilitates the formation of thin artificial muscles that are resistive to high voltage electrical breakdown and thus may operate at high voltages, facilitating an increase in achievable actuator force.

Referring still to FIGS. 9 and 10, the acryl-based polymer layer 154 is an adhesive layer (e.g., an acrylic adhesive emulsion) adhered to both the first electrode 106 and the BOPP layer 156. In some embodiments, the acryl-based polymer layer 154 comprises a poly(ethylacrylate acrylamide). However, it should be understood acryl-based polymer materials are contemplated, such as mono(ethylacrylate acrylamide), poly(methylacrylate acrylamide), mono (methylacrylate acrylamide), poly(proprylacrylate acrylamide), mono(proprylacrylate acrylamide), poly(butylacrylate acrylamide), mono(butylacrylate acrylamide), poly(pentylacrylate acrylamide), mono(pentylacrylate acrylamide), poly(hexylacrylate acrylamide), mono(hexylacrylate acrylamide), or the like.

In some embodiments, the one or more insulation layers 150 comprise a plurality of insulation bilayers 152 (FIG. 9) and in other embodiments, the one or more insulation layers 150 may comprise a single insulation bilayer 152 (FIG. 10). For example, in the embodiment depicted in FIG. 9, the first insulation layer 150a comprises a first insulation bilayer 152a comprising a first acryl-based polymer layer 154a disposed on the first electrode 106 and a first BOPP layer 156a disposed on the first acryl-based polymer layer 154a and the second insulation layer 150b comprises a second insulation bilayer 152b comprising a second acryl-based polymer layer 154b disposed on the first BOPP layer 156a and a second BOPP layer 156b disposed on the second acryl-based polymer layer 154b.

Referring still to FIGS. 9 and 10 the electrode insulator 113 may comprise a thickness $T_1$ of 50 µm or less, such as 45 µm or less, 40 µm or less, 35 µm or less, 30 µm or less, 25 µm or less, 20 µm or less, 15 µm or less, 10 µm or less, 5 µm or less, or any range having any two of these thicknesses as endpoints. Furthermore, in embodiments in which the one or more insulation layers 150 of the electrode insulator 113 comprise one or more insulation bilayers 152, the thickness of the acryl-based polymer layer 154 is greater than the thickness of the BOPP layer 156, for example 1.5-10 times thicker, such as 2-5 times thicker. Moreover, while not intending to be limited by theory, each insulation bilayer 152 comprises a breakdown voltage per thickness of 1 kV/µm or greater, 1.2 kV/µm or greater, 1.5 kV/µm or greater, 2 kV/µm or greater, or the like. Indeed, each insulation bilayer 152 comprises a breakdown voltage per thickness in a range of from 0.75 to 2.5 kV/µm, such as 0.8 kV/µm, 0.9 kV/µm, 1.0 kV/µm, 1.1 kV/µm, 1.2 kV/µm, 1.3 kV/µm, 1.4 kV/µm, 1.5 kV/µm, 1.6 kV/µm, 1.7 kV/µm, 1.8 kV/µm, 1.9 kV/µm, 2.0 kV/µm, 2.1 kV/µm, 2.2 kV/µm, 2.3 kV/µm, 2.4, kV/µm or any range having any two or these values as endpoints. While still not intending to be limited by theory, the breakdown voltage of the insulation bilayer 152 comprising the acryl-based polymer layer 154 and the BOPP layer 156, the thickness of the insulation bilayer 152 allows the artificial muscle 100' to be operated at increased voltages without shorting out, facilitating the formation of more powerful artificial muscles. For example, the insulation bilayer 152 is resistant to breakdown at voltages of 10 kV or greater, such as 11 kV or greater, 12 kV or greater, 15 kV or greater, 20 kV or greater, or the like.

While still not intending to be limited by theory, in operation, the actuator force applied by the artificial muscles 100' is inversely proportional to the thickness $T_1$ of the electrode insulator 113 and directly proportional to the applied voltage squared. Thus, reducing the thickness of the electrode insulator 113 while using materials that are resistant electrical shorting under large applied potentials, such as the acryl-based polymer layer 154 and the BOPP layer 156, facilitates an increase in the achievable actuator force. Moreover, as noted above, disposing the electrode insulator 113 on the first electrode 106 while leaving the second electrode 108 exposed to the dielectric fluid 198 further facilities reduced insulator thickness as this arrangement fortifies the artificial muscle 100' against electrical shorts caused by the stress induced reduction of the electrical breakdown voltage of the insulator materials.

Referring again to FIGS. 1-8, in order to move the first electrode 106 and the second electrode 108 of the artificial muscle 100, 100' toward one another, a voltage is applied by a power supply (such as power supply 408 of FIG. 11). The resulting attraction between the first electrode 106 and the second electrode 108 pushes the dielectric fluid 198 into the expandable fluid region 196. In the artificial muscle 100, pressure from the dielectric fluid 198 within the expandable fluid region 196 causes the first film layer 122 and the first electrode insulator 111 to deform in a first axial direction along the center axis C of the first electrode 106 and causes the second film layer 124 and the second electrode insulator 112 to deform in an opposite second axial direction along the center axis C of the second electrode 108. In the artificial muscle 100', pressure from the dielectric fluid 198 within the expandable fluid region 196 causes the first film layer 122 and the electrode insulator 113 to deform in a first axial direction along the center axis C of the first electrode 106 and causes the second film layer 124 to deform in an opposite second axial direction along the center axis C of the second electrode 108. With both artificial muscles 100, 100', once the voltage being supplied to the first electrode 106 and the second electrode 108 is discontinued, the first electrode 106 and the second electrode 108 return to their initial, non-parallel position in the non-actuated state.

It should be appreciated that the embodiments of the artificial muscle 100, 100' disclosed herein, specifically, the tab portions 132 with the interconnecting bridge portions 140, provide a number of improvements over actuators that do not include the tab portions 132, such as hydraulically amplified self-healing electrostatic (HASEL) actuators described in the paper titled "*Hydraulically amplified self-healing electrostatic actuators with muscle-like performance*" by E. Acome, S. K. Mitchell, T. G. Morrissey, M. B. Emmett, C. Benjamin, M. King, M. Radakovitz, and C. Keplinger (Science 5 Jan. 2018: Vol. 359, Issue 6371, pp. 61-65). Embodiments of the artificial muscle 100 including two pairs of tab portions 132 on each of the first electrode 106 and the second electrode 108, respectively, reduces the overall mass and thickness of the artificial muscle 100, reduces the amount of voltage required during actuation, and decreases the total volume of the artificial muscle 100 without reducing the amount of resulting force after actuation as compared to known HASEL actuators including donut-shaped electrodes having a uniform, radially-extending width. More particularly, the tab portions 132 of the artificial muscle 100 provide zipping fronts that result in increased actuation power by providing localized and uniform hydraulic actuation of the artificial muscle 100 compared to HASEL actuators including donut-shaped electrodes. Specifically, one pair of tab portions 132 provides twice the amount of actuator power per unit volume as compared to donut-shaped HASEL actuators, while two pairs of tab portions 132 provide four times the amount of actuator power per unit volume. The bridge portions 140 interconnecting the tab portions 132 also limit buckling of the tab portions 132 by maintaining the distance between adjacent tab portions 132 during actuation. Because the bridge portions 140 are integrally formed with the tab portions 132, the bridge portions 140 also prevent leakage between the tab portions 132 by eliminating attachment locations that provide an increased risk of rupturing.

In operation, when the artificial muscle 100, 100' is actuated by providing a voltage and applying the voltage to the electrode pair 104 of the artificial muscle 100, expansion of the expandable fluid region 196 produces a force of 5 Newton-millimeters (N·mm) per cubic centimeter ($cm^3$) of actuator volume or greater, such as 8 N·mm per $cm^3$ or greater, 10 N·mm per $cm^3$ or greater, 12 N·mm per $cm^3$ or greater, 15 N·mm per $cm^3$ or greater, 20 N·mm per $cm^3$ or greater, or the like. Providing the voltage may comprise generating the voltage, for example, in an embodiment in which the power supply 408 (FIGS. 4 and 11) is a battery, converting the voltage, for example in embodiment in which the power supply 408 (FIGS. 4 and 11) is a power adaptor, or any other known or yet to be developed technique for readying a voltage for application.

Moreover, the size of the first electrode 106 and the second electrode 108 is proportional to the amount of displacement of the dielectric fluid 198. Therefore, when greater displacement within the expandable fluid region 196 is desired, the size of the electrode pair 104 is increased relative to the size of the expandable fluid region 196. It should be appreciated that the size of the expandable fluid region 196 is defined by the central openings 146 in the first electrode 106 and the second electrode 108. Thus, the degree of displacement within the expandable fluid region 196 may alternatively, or in addition, be controlled by increasing or reducing the size of the central openings 146.

Referring now to FIG. 11, an actuation system 400 may be provided for operating the artificial muscles 100, 100'. The actuation system 400 may comprise a controller 410, an operating device 406, a power supply 408, a display device 402, network interface hardware 404, and a communication path 401 communicatively coupling these components. The controller 410 comprises a processor 412 and a non-transitory electronic memory 414 to which various components are communicatively coupled. In some embodiments, the processor 412 and the non-transitory electronic memory 414 and/or the other components are included within a single device. In other embodiments, the processor 412 and the non-transitory electronic memory 414 and/or the other components may be distributed among multiple devices that are communicatively coupled. The controller 410 includes non-transitory electronic memory 414 that stores a set of machine-readable instructions. The processor 412 executes the machine-readable instructions stored in the non-transitory electronic memory 414. The non-transitory electronic memory 414 may comprise RAM, ROM, flash memories, hard drives, or any device capable of storing machine-readable instructions such that the machine-readable instructions can be accessed by the processor 412. Accordingly, the actuation system 400 described herein may be implemented in any conventional computer programming language, as pre-programmed hardware elements, or as a combination of hardware and software components. The non-transitory electronic memory 414 may be implemented as one memory module or a plurality of memory modules. In some embodiments, the non-transitory electronic memory 414 includes instructions for executing the functions of the actuation system 400. The instructions may include instructions for actuating the artificial muscle 100.

The processor 412 may be any device capable of executing machine-readable instructions. For example, the processor 412 may be an integrated circuit, a microchip, a computer, or any other computing device. The non-transitory electronic memory 414 and the processor 412 are coupled to the communication path 401 that provides signal interconnectivity between various components and/or modules of the actuation system 400. Accordingly, the communication path 401 may communicatively couple any number of processors with one another, and allow the modules coupled to the communication path 401 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 11, the communication path 401 communicatively couples the processor 412 and the non-transitory electronic memory 414 of the controller 410 with a plurality of other components of the actuation system 400, such as the one or more sensors 405. For example, the actuation system 400 depicted in FIG. 11 includes the processor 412 and the non-transitory electronic memory 414 communicatively coupled with the operating device 406 and the power supply 408.

The operating device 406 allows for a user to control operation of the artificial muscle 100. In some embodiments, the operating device 406 may be a switch, toggle, button, or any combination of controls to provide user operation. The operating device 406 is coupled to the communication path 401 such that the communication path 401 communicatively couples the operating device 406 to other modules of the actuation system 400.

The power supply 408 (e.g., battery) provides power to the artificial muscle 100. In some embodiments, the power supply 408 is a rechargeable direct current power source. It is to be understood that the power supply 408 may be a single power supply or battery for providing power to the artificial muscles 100. A power adapter (not shown) may be provided and electrically coupled via a wiring harness or the like for providing power to the artificial muscle 100 via the power supply 408. Indeed, the power supply 408 is a device that can receive power at one level (e.g., one voltage, power level, or current) and output power at a second level (e.g., a second voltage, power level, or current).

In some embodiments, the actuation system 400 also includes a display device 402. The display device 402 is coupled to the communication path 401 such that the communication path 401 communicatively couples the display device 402 to other modules of the actuation system 400. The display device 402 may output a notification in response to an actuation state of the artificial muscle 100 or indication of a change in the actuation state of the artificial muscle 100. Moreover, the display device 402 may be a touchscreen that, in addition to providing optical information, detects the presence and location of a tactile input upon a surface of or adjacent to the display device 402. Accordingly, the display device 402 may include the operating device 406 and receive mechanical input directly upon the optical output provided by the display device 402.

In some embodiments, the actuation system 400 includes network interface hardware 404 for communicatively coupling the actuation system 400 to a portable device 470 via a network 460. The portable device 470 may include, without limitation, a smartphone, a tablet, a personal media player, or any other electric device that includes wireless communication functionality. It is to be appreciated that, when provided, the portable device 470 may serve to provide user commands to the controller 410, instead of the operating device 406. As such, a user may be able to control or set a program for controlling the artificial muscle 100 utilizing the controls of the operating device 406. Thus, the artificial muscle 100 may be controlled remotely via the portable device 470 wirelessly communicating with the controller 410 via the network 460.

It should now be understood that embodiments described herein are directed to artificial muscles that include an electrode insulator on the inner electrode surface of the first electrode while the inner electrode surface of the second electrode is a free inner electrode surface that faces the electrode insulator and is exposed to dielectric fluid when the artificial muscle is in a non-actuated state. Disposing the electrode insulator on only one of the pair of electrodes forms an electrode insulator asymmetry that mitigates the reduction the electrical breakdown voltage of material of the electrode insulator under stress and allows the artificial muscle to lift more weight with increased reliability against electrical breakdown shorts.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An artificial muscle comprising:
    a housing comprising an electrode region and an expandable fluid region;
    a dielectric fluid housed within the housing;
    an electrode pair positioned in the electrode region of the housing, the electrode pair comprising a first electrode and a second electrode; and
    an electrode insulator comprising one or more insulation layers, wherein:
        the electrode insulator is disposed on an inner electrode surface of the first electrode of the electrode pair;
        the second electrode comprises a free inner electrode surface exposed to the dielectric fluid when the electrode pair is in a non-actuated state; and
        the electrode pair is actuatable between the non-actuated state and an actuated state such that actuation from the non-actuated state to the actuated state directs the dielectric fluid into the expandable fluid region, expanding the expandable fluid region.

2. The artificial muscle of claim 1, wherein the free inner electrode surface of the second electrode is in an orientation facing the electrode insulator.

3. The artificial muscle of claim 1, wherein the one or more insulation layers of the electrode insulator comprise one or more insulation bilayers, each insulation bilayer comprising an acryl-based polymer layer disposed on the first electrode and a biaxially oriented polypropylene (BOPP) layer disposed on the acryl-based polymer layer.

4. The artificial muscle of claim 3, wherein the acryl-based polymer layer comprises a poly(ethylacrylate acrylamide).

5. The artificial muscle of claim 3, wherein the acryl-based polymer layer is an adhesive layer adhered to the first electrode and the BOPP layer.

6. The artificial muscle of claim 1, wherein the one or more insulation layers of the electrode insulator comprise a first insulation layer disposed on the inner electrode surface of the first electrode and the artificial muscle further comprises a second insulation layer disposed on the first insulation layer.

7. The artificial muscle of claim 6, wherein:
    the first insulation layer comprises a first insulation bilayer comprising a first acryl-based polymer layer disposed on the inner electrode surface of the first electrode and a first biaxially oriented polypropylene (BOPP) layer disposed on the first acryl-based polymer layer; and
    the second insulation layer comprises a second insulation bilayer comprising a second acryl-based polymer layer disposed on the first BOPP layer and a second BOPP layer disposed on the second acryl-based polymer layer.

8. The artificial muscle of claim 7, wherein the first acryl-based polymer layer and the second acryl-based polymer layer each comprise a poly(ethylacrylate acrylamide).

9. The artificial muscle of claim 1 wherein:
the first electrode and the second electrode each comprise two or more tab portions and two or more bridge portions;
each of the two or more bridge portions interconnects adjacent tab portions; and
at least one of the first electrode and the second electrode comprises a central opening positioned between the two or more tab portions and encircling the expandable fluid region.

10. The artificial muscle of claim 9, wherein the first electrode and the second electrode each includes two pairs of tab portions and two pairs of bridge portions, each bridge portion interconnecting adjacent a pair of adjacent tab portions, each tab portion diametrically opposing an opposite tab portion.

11. The artificial muscle of claim 1, wherein:
when the electrode pair is in the non-actuated state, the first electrode and the second electrode are non-parallel to one another; and
when the electrode pair is in the actuated state, the first electrode and the second electrode are parallel to one another, such that the first electrode and the second electrode are configured to zipper toward one another and toward the expandable fluid region of the housing when actuated from the non-actuated state to the actuated state.

12. The artificial muscle of claim 11, wherein when the electrode pair is in the actuated state, the electrode insulator contacts the free inner electrode surface of the second electrode.

13. A method for actuating an artificial muscle, the method comprising:
providing a voltage using a power supply electrically coupled to an electrode pair of an artificial muscle, the artificial muscle comprising:
a housing comprising an electrode region and an expandable fluid region, wherein the electrode pair is housed within the electrode region of the housing and comprises a first electrode and a second electrode;
a dielectric fluid housed within the housing; and
an electrode insulator comprising one or more insulation layers, wherein:
the electrode insulator is disposed on an inner electrode surface of the first electrode; and
the second electrode comprises a free inner electrode surface exposed to the dielectric fluid when the electrode pair is in a non-actuated state; and
applying the voltage to the electrode pair of the artificial muscle, thereby actuating the electrode pair from the non-actuated state to an actuated state such that the dielectric fluid is directed into the expandable fluid region of the housing and expands the expandable fluid region.

14. The method of claim 13, wherein the free inner electrode surface of the second electrode is in an orientation facing the electrode insulator.

15. The method of claim 13, wherein the one or more insulation layers of the electrode insulator comprise an insulation bilayer comprising an acryl-based polymer layer disposed on the first electrode and a biaxially oriented polypropylene (BOPP) layer disposed on the acryl-based polymer layer.

16. The method of claim 15, wherein the acryl-based polymer layer comprises a poly(ethylacrylate acrylamide).

17. The method of claim 15, wherein:
the one or more insulation layers of the electrode insulator comprise a first insulation layer disposed on the inner electrode surface of the first electrode and a second insulation layer disposed on the first insulation layer;
the first insulation layer comprises a first insulation bilayer comprising a first acryl-based polymer layer disposed on the first electrode and a first biaxially oriented polypropylene (BOPP) layer disposed on the first acryl-based polymer layer; and
the second insulation layer comprises a second insulation bilayer comprising a second acryl-based polymer layer disposed on the first BOPP layer and a second BOPP layer disposed on the second acryl-based polymer layer.

18. An artificial muscle comprising:
a housing comprising an electrode region and an expandable fluid region;
a dielectric fluid housed within the housing;
an electrode pair positioned in the electrode region of the housing, the electrode pair comprising a first electrode and a second electrode; and
an electrode insulator comprising one or more insulation layers, wherein:
the electrode insulator is disposed on an inner electrode surface of the first electrode;
the second electrode comprises a free inner electrode surface facing the electrode insulator; and
the electrode pair is actuatable between a non-actuated state and an actuated state such that actuation from the non-actuated state to the actuated state directs the dielectric fluid into the expandable fluid region, expanding the expandable fluid region.

19. The artificial muscle of claim 18, wherein:
the one or more insulation layers of the electrode insulator comprise a first insulation layer disposed on the inner electrode surface of the first electrode and a second insulation layer disposed on the first insulation layer;
the first insulation layer comprises a first insulation bilayer comprising a first acryl-based polymer layer disposed on the inner electrode surface of the first electrode and a first biaxially oriented polypropylene (BOPP) layer disposed on the first acryl-based polymer layer; and
the second insulation layer comprises a second insulation bilayer comprising a second acryl-based polymer layer disposed on the first BOPP layer and a second BOPP layer disposed on the second acryl-based polymer layer.

20. The artificial muscle of claim 18, wherein:
the first electrode and the second electrode each comprise two or more tab portions and two or more bridge portions;
each of the two or more bridge portions interconnects adjacent tab portions; and
at least one of the first electrode and the second electrode comprises a central opening positioned between the two or more tab portions and encircling the expandable fluid region.

* * * * *

UNITED STATES PATENT AND TRADEMARK OFFICE
CERTIFICATE OF CORRECTION

PATENT NO. : 11,696,821 B2
APPLICATION NO. : 17/218287
DATED : July 11, 2023
INVENTOR(S) : Michael P. Rowe and Maduran Palaniswamy It is certified that error appears in the above-identified patent and that said Letters Patent is hereby corrected as shown below:

In the Claims

In Column 15, Line(s) 1, Claim 9, after "claim 1", insert --,--.

Signed and Sealed this
Fifteenth Day of August, 2023

Katherine Kelly Vidal
*Director of the United States Patent and Trademark Office*